United States Patent [19]

Takami et al.

[11] Patent Number: 4,660,407
[45] Date of Patent: Apr. 28, 1987

[54] GAS SENSOR

[75] Inventors: Akio Takami; Toshitaka Matsuura; Akira Nakano; Yoshiaki Kuroki, all of Nagoya, Japan

[73] Assignee: NGK Spark Plug Co., Ltd., Nagoya, Japan

[21] Appl. No.: 762,385

[22] Filed: Aug. 5, 1985

[51] Int. Cl.⁴ ............................................. G01N 27/12
[52] U.S. Cl. ............................................ 73/23; 338/34
[58] Field of Search .................. 73/23, 27 R; 338/34; 422/98; 340/634

[56] References Cited

U.S. PATENT DOCUMENTS 4,414,531  11/1983  Novak .................................. 73/27 R Primary Examiner—Stephen A. Kreitman
Attorney, Agent, or Firm—Fleit, Jacobson, Cohn & Price

[57] ABSTRACT

A gas sensor has a ceramic substrate carrying a first ceramic layer formed thereon and a second ceramic layer formed on the first layer, the two layers having successive setbacks from one edge of the substrate so as to form a staircase-like edge structure, and a gas-sensitive layer is formed on the staircase-like edge portion of said substrate, height of said gas-sensitive layer above the substrate being less than the thickness of the first ceramic layer.

2 Claims, 19 Drawing Figures

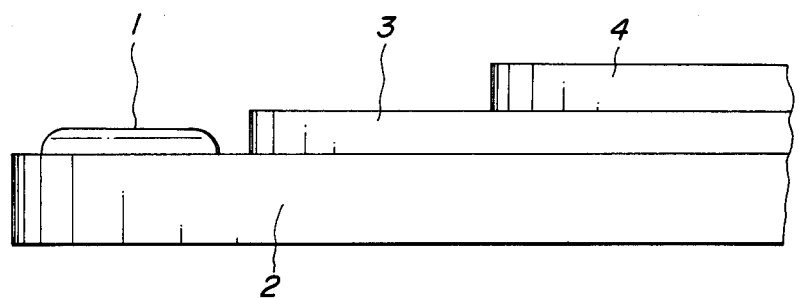
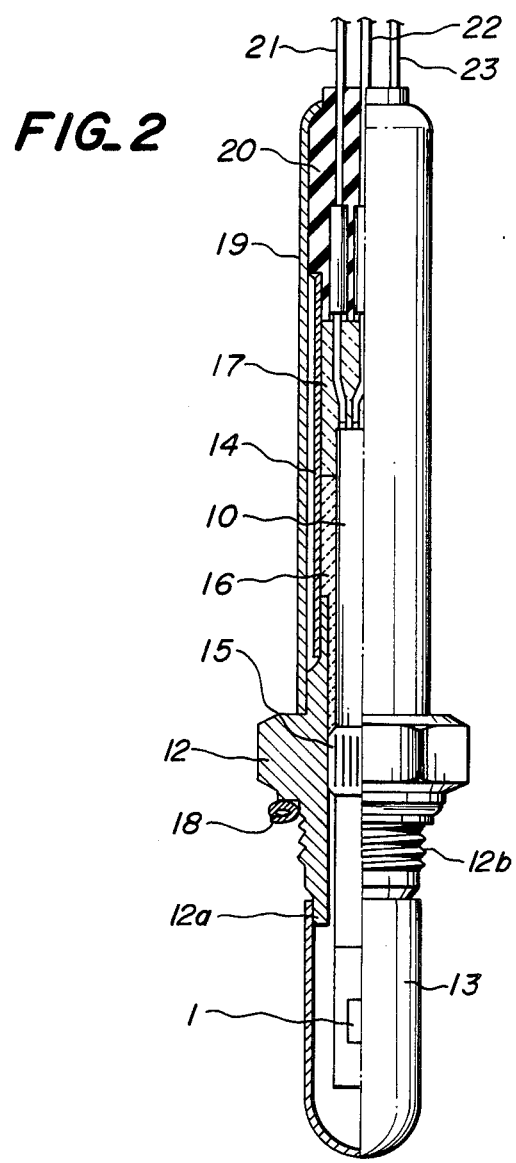

FIG. 3
FIG. 4
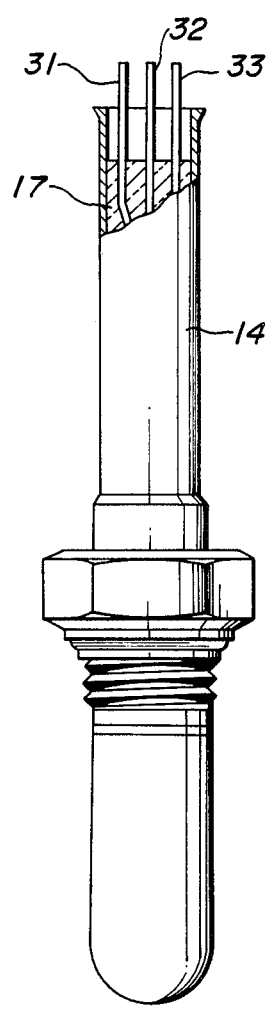
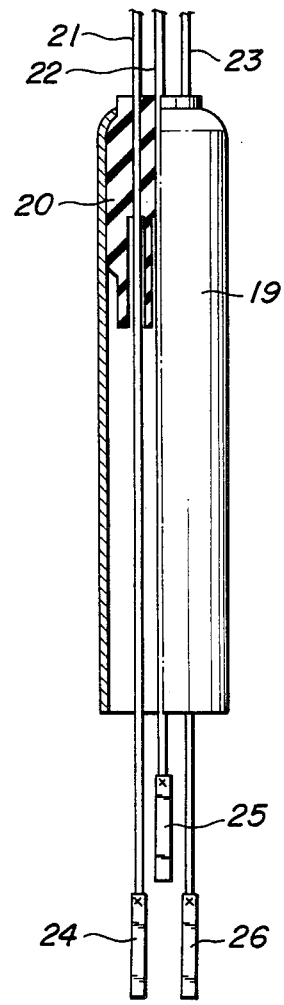

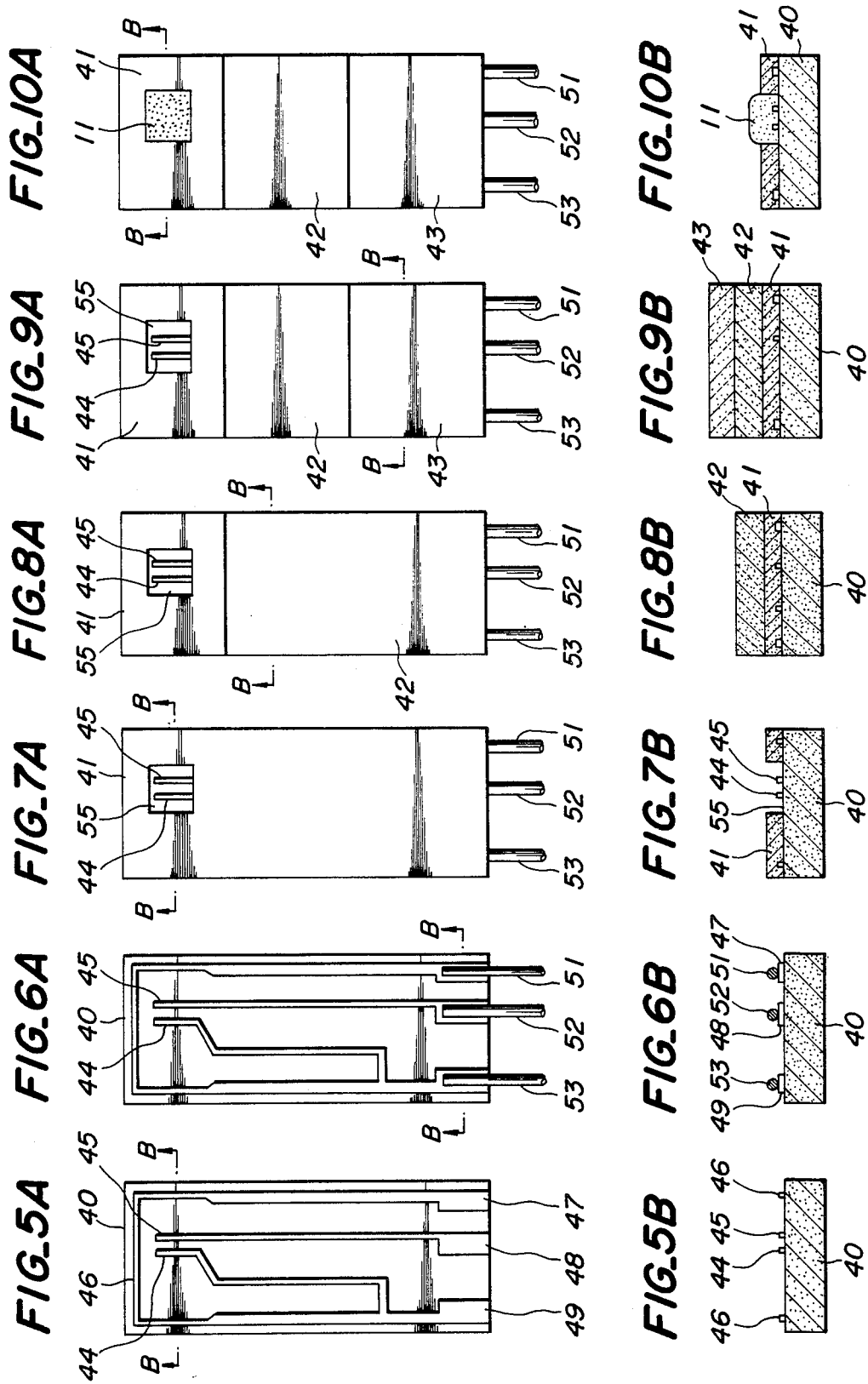

FIG_11A
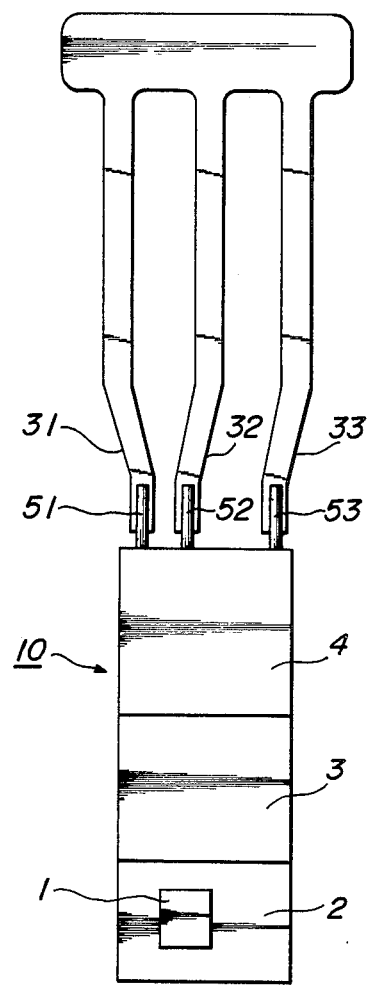
FIG_11B
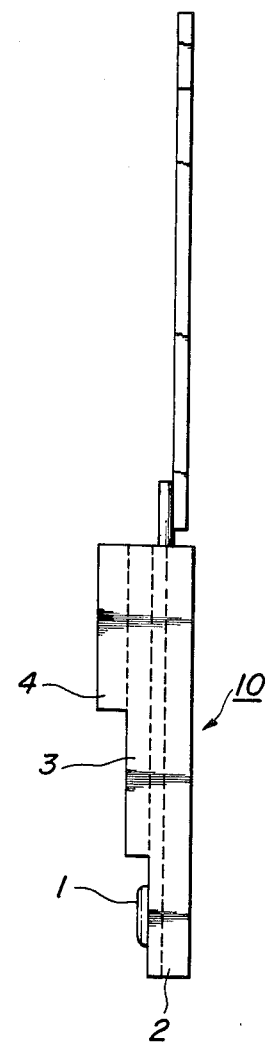

GAS SENSOR

BACKGROUND OF THE INVENTION

1. Field of the Invention

This invention relates to a gas sensor, and more particularly to a gas sensor for detecting a gaseous ingredient or its concentration.

2. Description of the Prior Art

It has been known to detect the presence and concentration of a gas in air by a gas sensor which uses a gas-sensitive element made of an oxide semiconductor, such as tin oxide ($SnO_2$), zinc oxide (ZnO), titania ($TiO_2$), cobalt oxide (CoO), and the like, whose electric resistance varies upon exposure to the gas. To simplify the structure of such gas-sensitive element for improving the productivity thereof, the so-called hybrid techniques has been developed; for instance, by printing both the gas-sensitive element and electrodes therefor in the form of thick films on an electrically insulating ceramic substrate.

To hold such a gas sensor in position for actual measurement, it has been practiced heretofore to put it in a housing which can be readily fixed at a location for detecting the object gas. However, certain difficulties have been experienced: for instance, that the gas sensor with the gas-sensitive element formed on the ceramic substrate has smooth surface with little undulations and it has been difficult to determine which part of the sensor be fixed to the housing with or without a spacer therebetween; and that, when a spacer is used between the housing and the gas sensor, the spacer tends to contact the gas-sensitive element and do harm to it during the assembling process, because the gas-sensitive element projects from the substrate for sensing the gas while the spacer keeps rather tight contact with the substrate for ensuring the secure holding.

SUMMARY OF THE INVENTION

Therefore, an object of the invention is to obviate the above-mentioned difficulties of the prior art by providing an improved gas sensor which can be easily mounted on a housing without any risk of harming the gas-sensitive element thereof during assembling. The structure of the gas sensor of the invention is such that, when a spacer is used between the housing and the gas sensor, which portion of the gas sensor be held by the spacer is easily determined and the risk of harming the gas-sensitive element by the spacer during the assembling is minimized.

To fulfil the above object, a gas sensor according to the invention uses a combination of a ceramic substrate and two ceramic layers formed thereon. More particularly, a first ceramic layer is formed on the ceramic substrate with a setback from one edge of the ceramic substrate, and a second ceramic layer is formed on the first ceramic layer with a setback from the setback portion of the first ceramic layer so as to form a staircase-like edge portion from said one edge of the substrate. Further, a gas-sensitive layer is formed on the staircase-like edge portion of the substrate in such a manner that the height of the gas-sensitive element above the ceramic substrate being smaller than thickness of the first ceramic layer.

Accordingly, when the gas sensor is assembled in a housing while using a spacer to provide a spacing therebetween, the step portion between the first ceramic layer and second ceramic layer in the staircase-like edge structure provides a position for secure engagement of the spacer with the gas sensor. Besides, the inside surface of the spacer thus engaging the first ceramic layer is prevented from coming in contact with the gas-sensitive layer on the surface of the ceramic substrate because the first ceramic layer is thicker than the height of the gas-sensitive layer above the surface of the ceramic substrate. Whereby, the gas-sensitive layer is protected against any harmful contact with the spacer during the assembling of the gas sensor in the housing.

BRIEF DESCRIPTION OF THE DRAWINGS

For a better understanding of the invention, reference is made to the accompanying drawings, in which:

FIG. 1 is a schematic partial side view showing the relationship among different layers in a gas sensor according to the invention;

FIG. 2 is a partially cutaway overall side view of an oxygen detector having an oxygen sensor embodying the invention mounted therein;

FIG. 3 is a partially cutaway side view of an inner cylinder of the oxygen detector, showing terminals extending outward from a glass seal of the inner cylinder;

FIG. 4 is a partially cutaway side view of an outer cylinder of the oxygen detector, showing the manner in which one end of the outer cylinder is closed by a sealing before it is coupled with the inner cylinder;

FIG. 5A, FIG. 6A, FIG. 7A, FIG. 8A, FIG. 9A and FIG. 10A are schematic plan views, showing the process in which a gas sensor of the invention is assembled;

FIG. 5B, FIG. 6B, FIG. 7B, FIG. 8B, FIG. 9B and FIG. 10B are sectional views taken along the lines with arrows B in FIG. 5A, FIG. 6A, FIG. 7A, FIG. 8A, FIG. 9A and FIG. 10A, respectively;

FIG. 11A is an explanatory diagram of the connections between lead wires and terminals;

FIG. 11B is a side view of FIG. 11A; and

Figure 12:
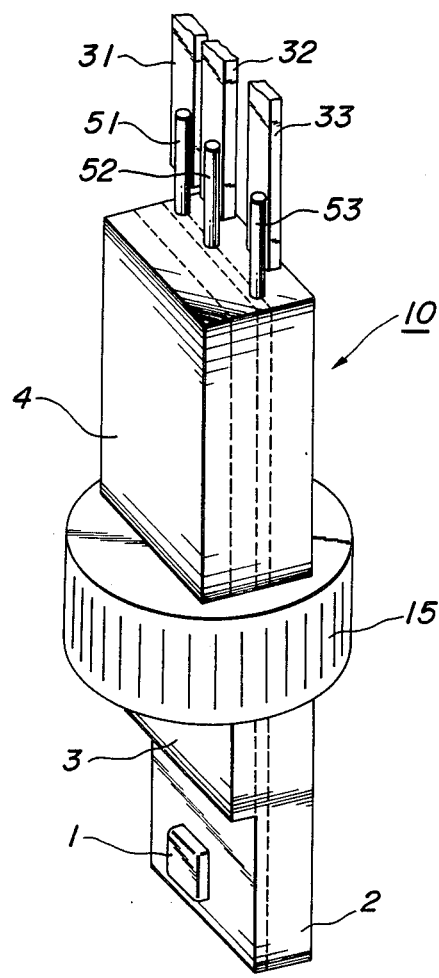
FIG. 12 is a schematic perspective view of the gas sensor of the invention with a spacer mounted thereon.

Throughout different views of the drawings, 1 is a gas-sensitive layer, 2 is a ceramic substrate, 3 is a first ceramic layer, 4 is a second ceramic layer, 10 is a gas sensor, 11 is gas-sensitive material, 12 is a body hardware, 13 is a protector, 14 is an inner cylinder, 15 is a spacer, 16 is filler powder, 17 is a glass seal, 18 is a gasket, 19 is an outer cylinder, 20 is a sealing, 21 through 23 are lead wires, 24 through 26 are compressible connectors, 31 through 33 are terminals, 40 is a ceramic substrate green sheet, 41 is a ceramic cover green sheet, 42 is a first ceramic layer green sheet, 43 is a second ceramic layer sheet, 44 and 45 are electrodes, 46 is a heater layer, 47 through 49 are end portions, 51 through 53 are platinum lead wires, and 55 is an opening.

DESCRIPTION OF THE PREFERRED EMBODIMENT

The detailed structure of the gas sensor according to the invention will be described now by referring to an embodiment illustrated in the accompanying drawings, which embodiment is an oxygen sensor for detecting the oxygen concentration in exhaust gas from an internal combustion engine.

Referring to FIG. 1, an essential feature of the gas sensor 10 of the invention is in that its gas-sensitive layer 1 is mounted on the staircase-like edge portion of a ceramic substrate 2. More particularly, a first ceramic layer 3 and a second ceramic layer 4 are overlaid on the substrate 2 while providing setbacks on the ceramic layers 3 and 4 relative to one edge of the substrate 2. Whereby, a staircase-like edge structure is formed at one end of the substrate 2. In the structure according to the invention, the first ceramic layer 3 must be thicker than the height of the gas-sensitive layer 1 from that surface of the substrate 2 which adjoins the first ceramic layer 3.

As can be seen from FIG. 12, when a spacer 15 is used to separate the gas sensor 10 from the inside surface of a body hardware 12 (FIG. 2), such spacer 15 is held at the step between the first ceramic layer 3 and the second ceramic layer 4 in the staircase-like edge structure. Whereby, the inside surface of the spacer 15 is prevented from coming into direct contact with the gas-sensitive layer 1, because the first ceramic layer 3 is thicker than the height of the gas-sensitive layer 1 above the substrate 2. Thus, the risk of harming the gas-sensitive layer 1 by such direct contact of the spacer 15 therewith is substantially eliminated.

In FIG. 2, showing a partially cutaway overall side view of an oxygen detector, a gas sensor 10 of the invention, in the form of an oxygen sensor, has a gas-sensitive layer 1 formed on a ceramic substrate. The gas sensor 10 of this embodiment detects the oxygen concentration of a gas being monitored. A cylindrical body hardware 12, which is mountable on an internal combustion engine, houses the gas sensor 10 thereon. A protector 13 is coupled to the engine-side end 12a of the body hardware 12, so as to protect the gas sensor 10. The gas sensor 10 is held by an inner cylinder 14 with a spacer 15 inserted therebtween, which inner cylinder 14 is carried by the body hardware 12. Filler powder 16 and glass seal 17 are stuffed between the gas sensor 10 and the inner cylinder 14, so as to keep the gas sensor 10 in position. To facilitate the mounting of the oxygen detector to an engine, the body hardware 12 has a threaded portion 12b. Thus, the oxygen detector can be screwed to the engine with a gasket 18 disposed between the body hardware 12 and the screwed portion of engine wall, so as to prevent engine exhaust gas from leaking through the screwed portion.

The filler powder 16, which is preferably a powder mixture consisting of talc and glass at a ratio of 1:1, acts to fix the gas sensor 10 in position within the inner cylinder 14. The glass seal 17 stuffed in the inner cylinder 14, which is preferably made of glass with a low melting point, acts to prevent the gas being monitored from leaking and to protect terminals of the gas sensor 10. To this end, the glass seal 17 covers and holds both a part of the gas sensor 10 and joints of the terminals with platinum lead wires to be described hereinafter.

An outer cylinder 19 is coupled to the body hardware 12 so as to cover the inner cylinder 14. A sealing 20 made of silicone rubber is stuffed in the outer cylinder 19 at the upper end thereof as shown in FIG. 4, so as to protect and insulate both outgoing lead wires 21 through 23 and their joints with the terminals 31 through 33 of the gas sensor 10 projecting from the glass seal 17 as shown in FIG. 2. To facilitate the joining of the lead wires 21 through 23 with the terminals 31 through 33 the sealing 20 and the lead wires 21 through 23 may be placed in the inside of the outer cylinder 19 beforehand, and compressible connectors 24 through 26 may be joined to the inner ends of the lead wires 21 through 23 respectively, as shown in FIG. 4. Then, the terminals 31 through 33 of the gas sensor 10 may be joined to the other ends of the connectors 24 through 26, respectively.

The inventors prepared a sample of the gas sensor 10 by a process as shown in the plan views of FIGS. 5A through FIG. 10A. FIG. 5B through FIG. 10B show sections taken along the lines with arrows B in FIG. 5A through FIG. 10A respectively. For clarity of the process of such preparation, the scale of the drawings of the gas sensor 10 in FIG. 5A through FIG. 10A is different from that of the above referred gas sensor 10 in FIG. 2 and from those of FIG. 11A and FIG. 12 to be explained later.

A ceramic substrate green sheet 40, a ceramic cover green sheet 41, a first ceramic layer green sheet 42, and a second ceramic layer green sheet 43 were formed in the following manner: Namely, 100 parts by weight of powder mixture was prepared by mixing 92% by weight (wt %) of alumina ($Al_2O_3$) with a mean diameter of 1.5 $\mu$m, 4 wt % of silica ($SiO_2$), 2 wt % of calcia ($CaO_2$), and 2 wt % of magnesia (MgO); 12 parts by weight of butyral resin and 6 parts by weight of dibutyl phthalate (DBP) were added to the 100 parts by weight of the powder mixture; a slurry was made by mixing the powder mixture after the above addition in an organic solvent; and the green sheets were formed from the slurry by using a doctor blade. The thickness of the green sheets was adjusted so as to produce the ceramic substrate green sheet 40 with a 1 mm thickness, the ceramic cover green sheet 41 with a 0.2 mm thickness, the first ceramic layer green sheet 42 with a thickness of 0.8 mm, and the second ceramic layer green sheet 43 was 0.8 mm thickness.

Electrically conductive layers 44 through 49 were printed in the form of thick film patterns, by using a platinum paste made by adding 7% of alumina ($Al_2O_3$) based on the amount of platinum. Of such conductive layers, electrodes 44 and 45 were for measuring the electric resistance of the above-mentioned gas-sensitive layer 1, and a heater layer 46 was for heating the gas-sensitive layer 1. End portions 47 through 49 were for applying an electric current to the heater layer 44 and extracting the output signal from the gas-sensitive layer 1.

In preparing the gas sensor 10, patterns for the electrodes 44, 45 and the heater layer 46 were at first printed on the ceramic substrate green sheet 40 together with their end portions 47 through 49 by using the platinum paste, a shown in FIG. 5A and FIG. 5B. Thereafter, platinum lead wires 51 through 53 with a diameter of 0.2 mm were disposed on the end portions 47 through 49 of the patterns respectively, as shown in FIG. 6A and FIG. 6B.

As shown in FIG. 7A and FIG. 7B, an opening 55 was bored, for instance by punching, through the ceramic cover green sheet 41 at such a position that, when the ceramic cover green sheet 41 with the opening 55 thus bored was overlaid in position on the ceramic substrate green sheet 40 so as to cover the entire pattern-printed surface of the latter sheet, the tip portions of the electrodes 44 and 45 were exposed to the outside through the opening 55. After being overlaid in the above manner, the ceramic cover green sheet 41 was joined to the ceramic substrate green sheet 40 by heating and pressing. In the illustrated embodiment, the lamination formed of the thus joined two green sheets 40 and 41 corresponded to the above-mentioned ceramic substrate 2 of FIG. 1. Gas-sensitive material 11 was deposited in the opening 55 so as to provide the above-mentioned gas-sensitive layer 1 of FIG. 1.

Referring to FIG. 8A and FIG. 8B, the first ceramic layer green sheet 42 was overlaid on the ceramic cover green sheet 41 of the above lamination and joined thereto by heating and pressing. A setback was provided in the first ceramic layer green sheet 42 as shown in FIG. 8A. Thereafter, the second ceramic layer green sheet 43 was overlaid on the joined to the first ceramic layer green sheet 42 by heating and pressing while forming a setback relative to the latter green sheet as shown in FIG. 9A and FIG. 9B. Whereby, a staircase-like edge structure was formed at one end of the ceramic substrate green sheet 40. In this case, the green sheets 42 and 43 thus joined to the green sheets 41 corresponded to the above-mentioned first ceramic layer 3 and the second ceramic layer 4 of FIG. 1 respectively.

Thus, the printed patterns for the electrodes 44, 45 and the heater layer 46 were sandwiched between the green sheets 40 and 41, with the platinum lead wires 51 through 53 partially projecting to the outside of the thus joined green sheets 40 and 41 and with the tip portions of the electrodes 44 and 45 being exposed to the outside through the opening 55, and a green lamination with the staircase-like edge structure was formed by joining the ceramic layer green sheets 42 and 43 to the above green sheets 40 and 41 in the aforesaid manner. The green lamination was fired at 1,500° C. in air for two hours so as to provide the ceramic substrate 2 carrying the ceramic layers 3 and 4 laminated thereon.

As shown in FIG. 10A and FIG. 10B, gas-sensitive material 11 was deposited on the fired ceramic substrate 2 through the opening 55 of its cover layer formed of the ceramic cover green sheet 41. To this end, a titania paste was prepared in the following manner; namely, 1 mole part of platinum black was mixed in 100 mole parts of titania ($TiO_2$) powder having a mean diameter of 1.2 $\mu$m; 3 Wt % of ethyl cellulose based on the total of the powder mixture was added therein; and the mixture thus prepared was further mixed in BUTYL CARBITOL (a merchandise mark of 2-(2-butoxy ethoxy) ethanol) while controlling its viscosity so as to produce the titania paste having a viscosity of 300 poise.

The titania paste was applied to the opening 55 by the thick film techniques so as to fill up the opening 55 while ensuring tight contact of the tip portions of the electrodes 44 and 45 with the titania paste. The ceramic lamination with the titania paste applied thereon was fired at 1,200° C. in air for one hour, so that the gas-sensitive layer 1 was formed as overlaid on the ceramic substrate 2. Whereby, a sample of the gas sensor 10 according to the invention was completed. It should be noted here that the thickness of the first ceramic layer 3 made by firing the first ceramic layer green sheet 42 was thicker than the height of gas-sensitive element 1 from that surface of the ceramic substrate 2 which adjoined the first ceramic layer 3. In fact the above-mentioned height was less than 0.3 mm.

The platinum lead wires 51 through 53 extending outwardly from the gas sensor 10 were connected to the terminals 31 through 33 respectively in a manner as shown in FIG. 11A. FIG. 11B shows a side view of the illustration of FIG. 11A. The terminals 31 through 33 were made by etching a 0.3 mm thick nickel plate without severing them from each other as shown in FIG. 11A. The terminals 31 through 33 were brought in contact with the platinum lead wires 51 through 55 respectively, and the portions in contact with each other were bonded by welding. The gas sensor 10 thus provided with the terminals was placed in the inner cylinder 14 carried by the body hardware 12 as shown in FIG. 3, so that the joint portions between the platinum lead wires 51 through 53 and the terminals 31 through 33 respectively were protected by the glass seal 17 fitted in the inner cylinder 14. Then, the three terminal 31 through 33 were severed from each other at suitable portions so as to provide the terminals of certain lengths.

As described in the foregoing, the gas sensor 10 according to the invention has a staircase-like edge structure at that end of the ceramic substrate 2 which carries the gas-sensitive layer 1, so that when a spacer 15 is mounted on the gas sensor 10 of the invention, the spacer 15 is readily positioned in a reliable manner at the step between the first ceramic layer 3 and the second ceramic layer 4 of the staircase-like edge structure as shown in FIG. 12. The ceramic layers 3 and 4 of the illustrated embodiment were made by using the green sheets 42 and 43 as explained above in detail.

Besides, that portion of the gas sensor 10 which engages the inside surface of the spacer 15 is thicker than the height of the gas-sensitive layer 1 from the bottom of the gas sensor 10, so that the inside hole of the spacer 15 is larger than the gas-sensitive-layer-carrying portion of the gas sensor 10 and the spacer 15 can be easily mounted on the gas sensor 10 without touching the gas-sensitive layer 1. Accordingly, the efficiency in the work of mounting the gas sensor 10 on the body hardware 12 is improved and the risk of harming the gas-sensitive layer 1 during such mounting is substantially eliminated.

In the case of the oxygen sensor which has been described above as an embodiment of the invention, a power source voltage for heating is applied across the lead wires 21 and 23 so as to heat up the heater layer 46 for activating the gas-sensitive layer 1. The oxygen concentration can be determined by measuring the electric resistance across the lead wires 22 and 23, and change of the oxygen concentration can be monitored by measuring variations in the above electric resistance.

As described in the foregoing, a gas sensor according to the invention has a staircase-like edge structure at one end of the ceramic substrate, said structure being made of a gas-sensitive-layer-carrying end of the substrate, a first ceramic layer overlaid on the substrate with a setback from the gas-sensitive layer, the first ceramic layer being thicker than the height of the gas-sensitive layer above the substrate, and a second ceramic layer overlaid on the first ceramic layer with a setback therefrom. Whereby, when the gas sensor is mounted on a housing or fixed to an object, the positioning of the gas sensor can be easily effected by using the step between the first ceramic layer and the second ceramic layer, so that the mounting or the fixing of the gas sensor can be carried out efficiently.

Since the first ceramic layer is thicker than the height of the gas-sensitive layer over the ceramic substrate, when a spacer is used to facilitate the mounting of the gas sensor on a housing or the like, the spacing is prevented from coming in direct contact with the gas-sensitive layer and harming such gas-sensitive layer.

Further, the gas sensor of the invention has a thick end and a thin end with the gas-sensitive layer, and if its thick end is held by the housing or the like so as to extend the thin end into a measuring atmosphere, the heat capacity of the gas-sensitive portion is kept small for providing fast response by facilitating quick temperature rise of the gas-sensitive layer while ensuring steady holding of the gas sensor itself.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A gas sensor comprising a ceramic substrate, a first ceramic layer formed on the ceramic substrate, with a setback from one edge of the ceramic substrate, a second ceramic layer formed on the first ceramic layer with a setback from the setback portion of the first ceramic layer so as to form a staircase-like edge structure at said one edge of the substrate, and a gas-sensitive layer formed on the staircase-like portion of the substrate, height of said gas-sensitive layer above said substrate being smaller than thickness of said first ceramic layer.

2. A gas sensor as set forth in claim 1, wherein said gas sensor further comprises a heater layer secured to the ceramic substrate so as to heat the gas-sensitive layer.

* * * * *